(12) United States Patent
Wokal

(10) Patent No.: US 6,202,345 B1
(45) Date of Patent: Mar. 20, 2001

(54) SUPPORT STRUCTURE FOR ATTACHMENT TO AUTOMOTIVE CIGARETTE LIGHTER RECEPTACLE

(76) Inventor: Gary Wokal, P.O. Box 832, Carpenteria, CA (US) 93014

( * ) Notice: Subject to any disclaimer, the term of this patent is extended or adjusted under 35 U.S.C. 154(b) by 0 days.

(21) Appl. No.: 09/339,717

(22) Filed: Jun. 24, 1999

(51) Int. Cl.[7] .................................................. A01G 9/02
(52) U.S. Cl. .............................................. 47/41.01; 47/15
(58) Field of Search ............................ 47/41.11, 41.14, 47/41.13, 41.01, 41.15; 248/311.2, 314, 231.9

(56) References Cited

U.S. PATENT DOCUMENTS

| | | |
|---|---|---|
| D. 296,928 | 7/1988 | Lee et al. |
| D. 365,041 | 12/1995 | Dollinger . |
| 522,910 | 7/1894 | Marston . |
| 1,096,180 * | 5/1914 | Meurling .................... 47/41.11 X |
| 1,379,340 | 5/1921 | Hegamin . |
| 2,756,542 | 7/1956 | Mossman . |
| 3,056,969 | 10/1962 | Speros . |
| 3,610,917 | 10/1971 | Hunt . |
| 3,704,776 | 12/1972 | Collins . |
| 4,418,496 | 12/1983 | Koistinen . |
| 4,877,164 * | 10/1989 | Baucom ............................. 224/42.44 |
| 5,048,733 * | 9/1991 | Nagy ................................. 224/42.42 |
| 5,060,417 | 10/1991 | Court . |
| 5,086,958 * | 2/1992 | Nagy ................................... 248/311.2 |
| 5,106,046 * | 4/1992 | Rowles et al. .................... 248/311.2 |
| 5,361,950 * | 11/1994 | Signal et al. ................... 248/311.2 X |
| 5,456,046 * | 10/1995 | Vitalune et al. .................... 47/41.01 |
| 5,462,212 * | 10/1995 | Hertel, Jr. ............................. 224/570 |
| 5,489,055 * | 2/1996 | Levy .............................. 248/311.2 X |
| 5,579,928 * | 12/1996 | Anukwuem ............................ 211/74 |
| 5,938,160 * | 8/1999 | Hartmann et al. ................ 248/311.2 |
| 5,961,207 * | 10/1999 | Petkovic ................................ 362/376 |
| 5,991,646 * | 11/1999 | Frank et al. .......................... 455/569 |

OTHER PUBLICATIONS

Author Unknown p. 206 HMN, Jan. 1999 Advertisement.

* cited by examiner

Primary Examiner—Peter M. Poon
Assistant Examiner—Jeffrey L. Gellner
(74) Attorney, Agent, or Firm—Gene W. Arant

(57) ABSTRACT

A holding device which can be attached to a standard cigarette lighter receptacle which is located in the dashboard of an automobile.

The holding device comprises: 1) a support member which is inserted into the cigarette lighter receptacle; and 2) an elongated holding member which can accept an object such as a cigar for storage; or a test-tube shaped container which is capable of holding water and one flower or a small floral arrangement.

The elongated holding member can have various artistic designs on its outer wall surface which will add to the pleasing aesthetics of the holder in an automobile.

1 Claim, 3 Drawing Sheets

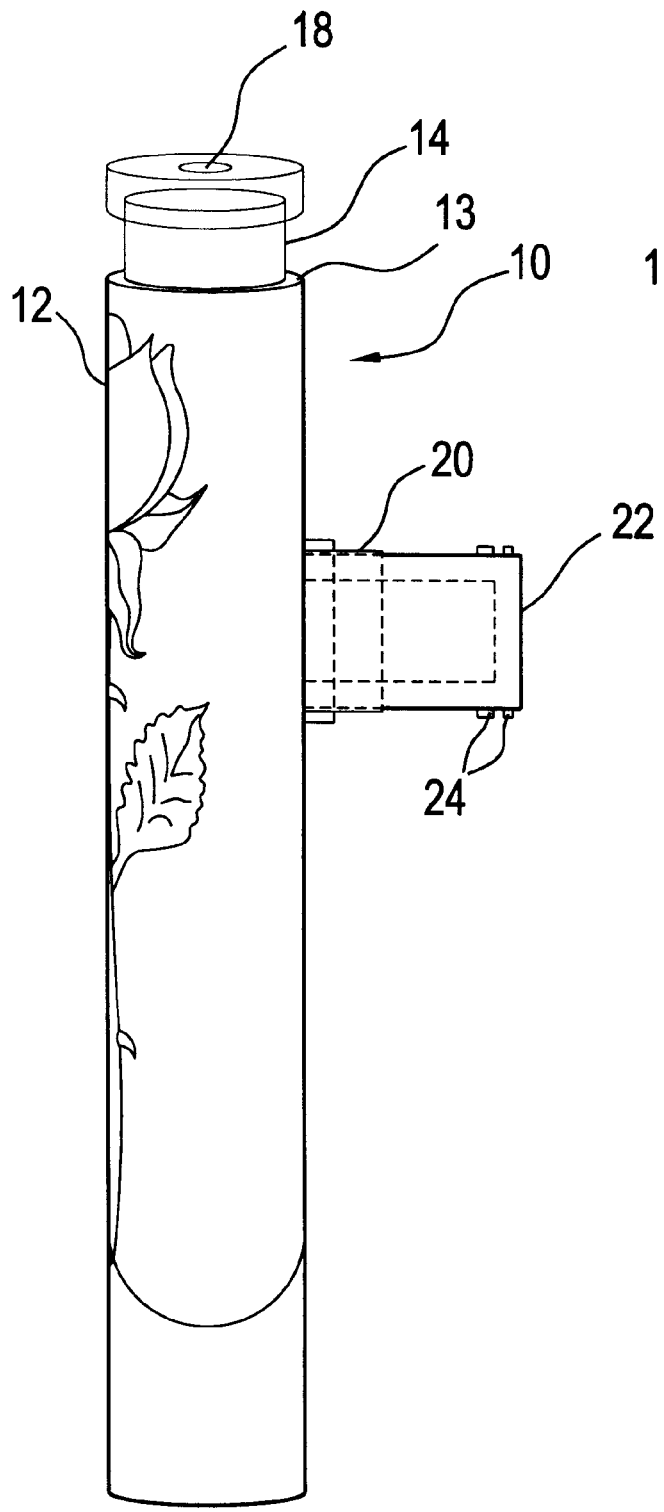
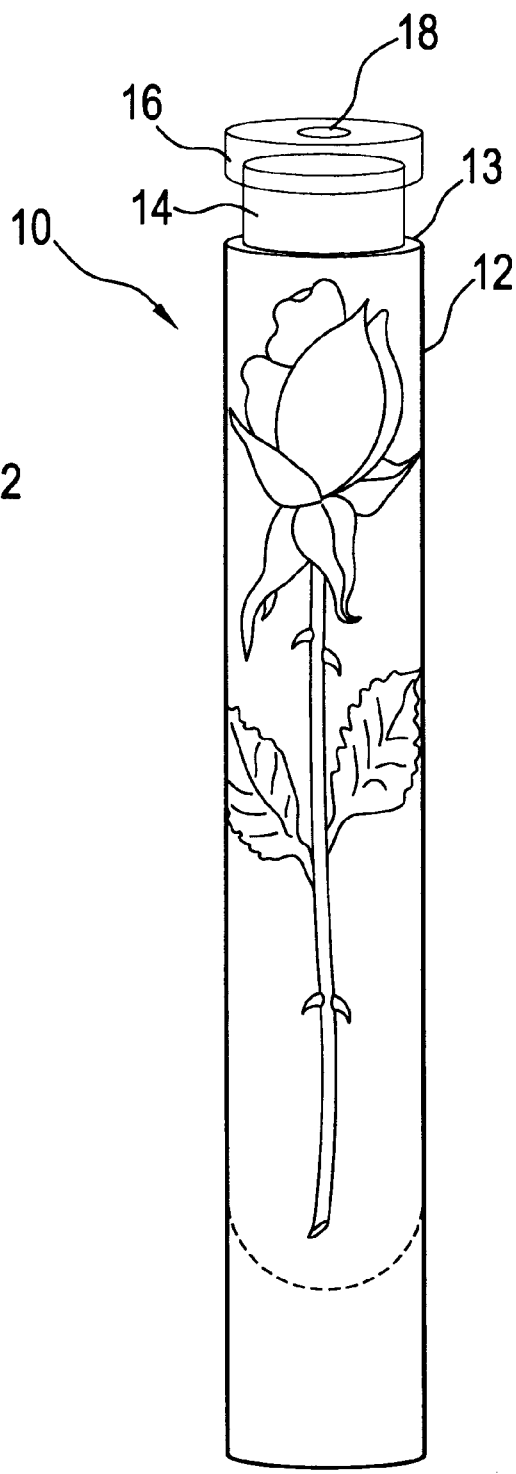

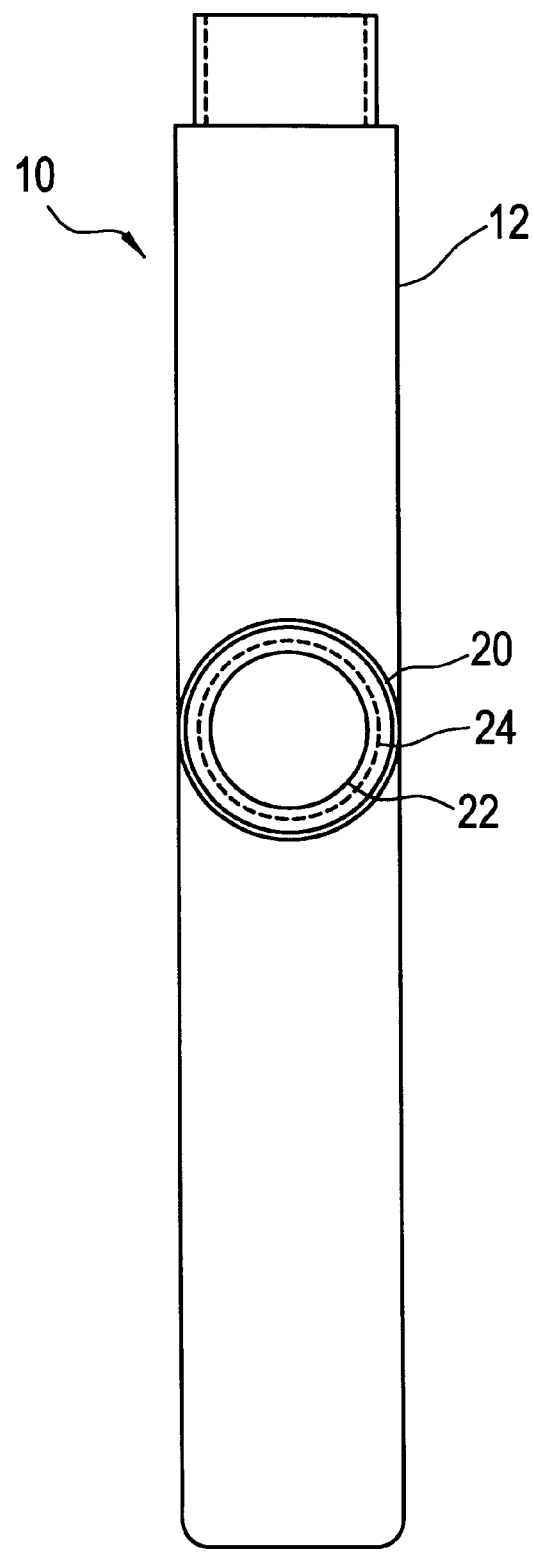

SUPPORT STRUCTURE FOR ATTACHMENT TO AUTOMOTIVE CIGARETTE LIGHTER RECEPTACLE

FIELD OF INVENTION

The present invention relates to a structure for supporting objects within the passenger cabin of an automobile for providing pleasing aesthetics to obtain a level of calmness while driving and to provide a natural fresh scent.

BACKGROUND

Automobiles are designed so that the driver and any passengers are seated in a compartment which is usually an enclosed space having exterior doors and windows.

In order to circulate air, vents, and sometimes air conditioning is provided. Besides having fresh air circulated into the passenger cabin of an automobile, the driver or passengers may sometimes prefer that the air be scented with a desired fragrance for providing a more appealing smell for the passengers and driver.

Different varieties of air fresheners are available for use in an automobile. Air fresheners range from simple aerosol spray to scented items which usually hang on the rear-view mirror.

These air fresheners usually consist of an imitation odor such as "new-car", pine or other scent.

Many years ago, the prior art included a receptacle mounted to the dashboard of an automobile for the placing of a flower and stem.

However, the prior art does not address a device which is connected to a standard cigarette lighter receptacle which would allow the placement of fresh flowers in the cabin of an automobile to be used not only as an air freshener but also as a decorative ornament.

Receptacles for receiving flowers and temporarily fixing the position of the flowers relative to a structure is well known in the prior art.

For example, U.S. Pat. No. 4,418,496 issued to Koistinen, discloses a support structure for small floral arrangements for use at weddings which utilize a multipurpose hanger.

It is therefore an object of the invention to provide a holder which can be temporarily attached to the cigarette lighter receptacle of an automobile which will permit the placement of a flower within the cabin of an automobile for aesthetic beauty as well as for the pleasant scent it will provide to the interior cabin space.

It is further an object of the invention to provide a holder which, instead of a holding flower, can be used for holding a cigar within the cabin of an automobile.

It is also an object of the invention to design the holder so it can be manufactured easily and inexpensively.

SUMMARY OF THE INVENTION

My invention is a holder which can be attached to an automobile's cigarette lighter receptacle that is part of a car's dashboard. The holder is sufficiently rigid so it can support the weight of an object placed inside without substantial deformation.

The preferred use of my invention will be to hold a single flower or small floral arrangement. A flower or flowers, with stems inserted into the holder, will provide a fresh scent and aesthetic beauty to the interior cabin of an automobile and which will be in plain sight of the driver. Alternatively, the holder can also be utilized for placement of an expensive cigar therein and utilize an optional cover to preserve the freshness of the cigar. The purpose of my invention is thus to provide an attractive yet unobtrusive, stationary, and spill-proof vase suitable for prominently displaying a flower or small floral arrangement within the passenger cabin of an automobile so as to artistically enhance and beautify its interior, stimulate the passengers' visual and olfactory senses, and effect calmness by imparting the scents and visual aesthetics of nature into the passengers' automotive environment.

VARIED EMBODIMENTS

The holder can either be of single piece construction or made of two or more separate sections. The following embodiments are considered as part of my invention:

A. Integral Section and Glass Holder.

The holder comprises two pieces: 1) a test-tube shaped member capable or retaining water; and 2) an integral body having two sections; the first section being a elongated holding member for receiving the test-tube shaped member and the second section being a support member extending perpendicularly away from the first section.

The support member has a male distal first end that is designed to be inserted within an automobile's cigarette lighter receptacle temporarily securing the holder in a fixed position relative to the automobile dashboard.

The test-tube shaped member can be made of plastic but more preferably, it is made of tempered glass such as PYREX® and can be removed from the elongated holding member. Since my invention anticipates holding a flower stem and water, over time algae and possibly mold and bacteria will grow if the holder is not periodically cleaned. A tempered glass test-tube is preferred because of its durability and also for its ease of cleaning. The test-tube member can be removed from the elongated holding member, and cleaned. The test-tube member can thereafter be re-inserted into the elongated holding member for subsequent use.

The integral body is preferably made of a plastic material such as polyurethane although any material may be used so long as it serves reduce the chances of damage such as breakage to the test-tube member while within the elongated member.

Various artistic designs can be etched, painted, engraved, embossed, or stenciled onto the elongated holding member. The elongated holding member can also be made in different colors and exterior circumferential shapes; all to provide aesthetic pleasure to the viewer.

Although the integral body, which comprises the elongated holding member and support member, is preferably made of a plastic material, each member can be made of differing or multiple materials and permanently bonded or connected to one another.

For example, the elongated holding member, may be made of copper having decorative etched designs on its outer wall, while the support member is made of plastic and bonded to a portion of the elongated holding member. Other materials of construction for the elongated holding member include wood and aluminum.

B. Integral Section Only.

The holder is comprised of a single piece having two sections; the first section being an elongated holding member having a hollow interior and an aperture so that objects can be inserted into the hollow interior; and the second section being a support member extending perpendicularly away from the holding member. The support member has a distal first end that can be inserted within an automobile's cigarette lighter receptacle temporarily securing the holder in a fixed position relative to the automobile dashboard.

As for embodiment "A" described above, the elongated holding member may include artistic designs and may even be made of a different material than the support member.

C. Multiple Sections and Glass Holder.

In this embodiment, my invention comprises three sections: 1) a test-tube shaped member preferably made of tempered glass such as PYREX®; 2) a elongated holding member into which the test-tube shaped member can be inserted and removed; and, 3) a support member. The support member has a distal male end that can be inserted and temporarily secured within an automobile's cigarette lighter receptacle.

A means is utilized to connect the support member to the elongated holding member. Any number of embodiments can be employed as a functional connecting means. Such embodiments include but are not limited to the following:

1. Support member having a second end comprising two prongs which frictionally engage the circumference of the elongated holding member;
2. Support member having a second end comprising a male threaded end for engagement with a female threaded end positioned on said elongated holding member;
3. Support member having female threaded end for threadably engaging a threaded male end located on the elongated holding member; or
4. The elongated holding member having a tapered outer circumference distant from the aperture opening and the support member having a ring end so that the tapered end of the elongated holding member can be partially inserted into the ring end of the horizontal member until frictional contact is obtained.

The most desired feature of the connecting means is that the elongated holding member and support sections can be assembled and disassembled quickly and repeatedly. The disassembled unit provides for more compact storage than an assembled holder.

Further, the male end of the support member which is inserted into the cigarette lighter receptacle is made of non-conductive material, preferably a plastic material such a polyurethane.

Because of the various dash designs and cigarette lighter locations, support members of various length can be manufactured and thereafter selected for optimum positioning of the test-tube member and elongated holding member relative to the dashboard.

As for embodiment "A" described above, the elongated holding member may include artistic designs and be even made of a different material than the support member.

D. Multiple Sections without Glass Holder.

This embodiment is the same as embodiment "C" but without the glass test-tube member.

GENERAL CONFIGURATION OF INVENTION

In its assembled condition, the holder is generally either of an "L"-shaped or "T"-shaped configuration. The support member extends perpendicularly away from the elongated holding member.

The distal end of the support member has an outer circumference for engaging a portion of the inner circumference of a standard cigarette lighter receptacle. In one embodiment, the distal end has one or more pliable rings about the circumference of the support member which have an outside diameter slightly larger than the inside diameter of a cigarette lighter receptacle. When the distal end of the support member is inserted into the cigarette lighter receptacle, the rings will deform slightly and frictionally engage the receptacle.

The support member may thereafter be rotated as necessary so that the elongated holding member section will be in a vertical position. Frictional engagement of the support member to the receptacle also fixes the position of the holder relative to the dashboard.

The pliable rings located on the support member are designed to frictionally engage temporarily to the cigarette lighter receptacle and the support member may be removed from the receptacle by an individual applying the necessary force to overcome the frictional engagement.

It should be noted that a frictional engagement is desired and any suitable design which achieves this purpose is envisioned by my invention.

The distal end of the support member can be of any configuration so long as it is capable of frictionally engaging the interior of a cigarette lighter receptacle and can be removed as desired by an individual.

However, some automobile dashboards have a curved surface from the position of the cigarette lighter receptacle to the top of the dashboard. In these situations, the support member may be designed to include a rigid center portion which is curved to follow the curvature of the dashboard, or alternatively, a deformable center portion which can be adjusted into any desired contour.

Optionally, a top plug, made of rubber or similar material, is provided for insertion into the top of the test tube member. The top plug has a center aperture and its purpose is two-fold. First, it reduces the opening into the test tube thereby preventing inadvertent spillage of water from the test tube to the interior of the car. Second, the center aperture has a diameter sized slightly larger than a flower stem to permit a single flower stem to pass through and yet provide support to maintain the flower bloom in substantially vertical position.

An alternative use for the holder is that it can be used without the test-tube member as in embodiments "B" and "D", as a container to hold a single cigar. This alternative use would then incorporate a top cover to seal the cigar within the elongated first section for maintaining the freshness of a cigar.

DESCRIPTION OF THE DRAWINGS

FIG. 1 is a front view of the invention.

FIG. 2 is a side view of the invention.

FIG. 3 is a rear view of the invention.

DETAILED DESCRIPTION OF THE PREFERRED EMBODIMENT

Figure 4:
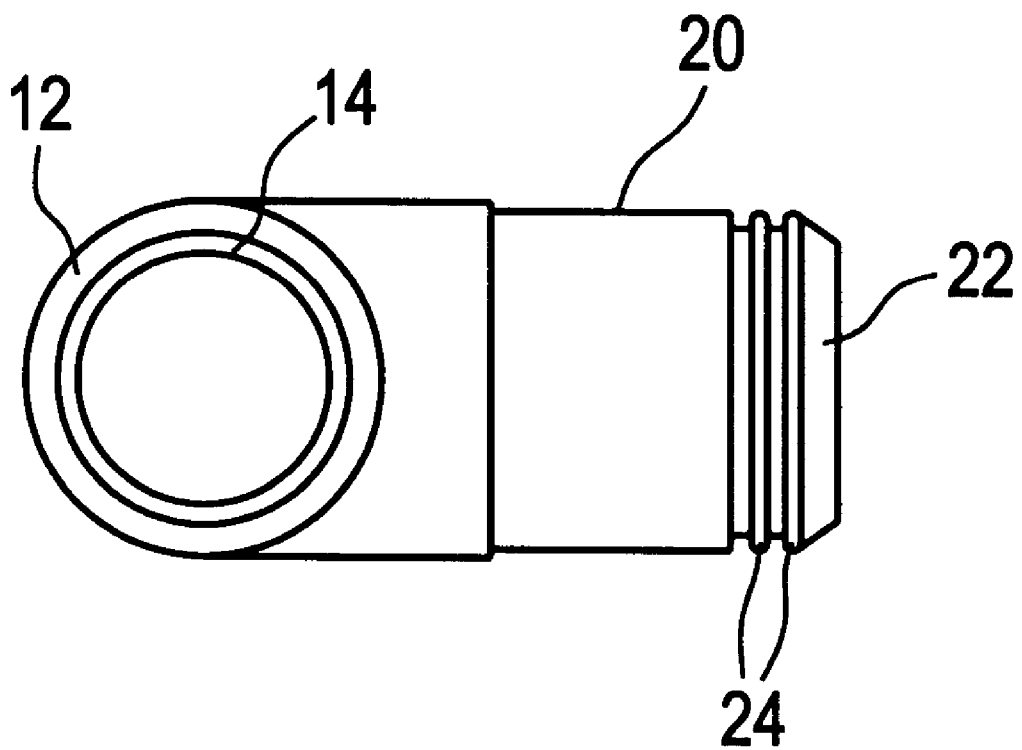
FIG. 4 is a top view of the invention.

My invention 10 is illustrated in FIGS. 1–4 and comprises an elongated hollow member 12 having aperture 13. The diameter of the hollow space of elongated member 12 is sufficient for test-tube member 14 to be slid into. Optionally, either a cap 16 or a plug (not shown) can be used to temporarily reduce the aperture opening of test-tube 14. Either cap 16 or plug (not shown) would include an aperture 18. Connected to elongated member 12 is support member 20. The distal end of support member 20 comprises male end 22 having frictional ribs 24.

With the main parts of my invention identified, I will now describe each part in greater detail.

Elongated hollow member 12 can be comprised of any material which is capable of protecting test-tube 14 from breakage such as plastic and more preferably polyurethane. Invention 10 can also be utilized as a decorative item. To this end, elongated member 12 can also be made of such material as copper or wood and can include etching or embossing design work on the exterior surface. The outside dimensions of elongated member 12 are not critical. The critical parameters however, are that the diameter of aperture 13 be sufficient to permit test-tube 14 to be slid into the hollow interior and further that the hollow space of elongated member 12 is sufficient to permit test-tube 14 to either be completely slid or substantially slid into its hollow space.

Test-tube member 14 is preferably made of tempered glass such as PYREX®. Test-tube 14 can be periodically removed from elongated member 12 and cleaned. Test-tube 14 can also include a lip ring around its aperture end. For this embodiment, cap 16 can be utilized to frictionally engage the lip area and maintain itself on the end of test-tube 14. Alternatively, a plug can be use instead of cap 16, whether test-tube 14 has a lip ring or not.

The purpose of either cap 16 or plug (not shown) is to reduce spillage of water from test-tube 14 and also to provide some support for a flower stem.

Support member 20 is preferably connected permanently to elongated member 12, in a perpendicular relationship. This can be done using adhesives or the like. Alternatively, elongated member 12 and support member 20 may be constructed integrally such as by injection molding. Male end 22 is sized to be inserted into a standard cigarette lighter receptacle and friction ribs 24 are sized to frictionally engage a portion of the inside circumferential area of the receptacle. Male end 22 is preferably made of a non-conductive material such as polyurethane. Friction ribs 24 are designed to secure attachment to the inner wall of the receptacle until sufficient pulling force is applied for removal.

With the invention described, its operation will now be discussed.

Male end 22 of support member 20 is inserted into a cigarette lighter receptacle. Friction ribs 24 will engage a portion of the inside circumferential area of the receptacle. Elongated member 12 is connected to the end of support member 20 distal from male end 22. It is desired to position elongated member 12 so it will be essentially vertical. Because of the perpendicular relationship of elongated member 12 to support member 20, support member 20 may have to be rotated slightly to achieve a vertical position for elongated member 12.

Test-tube 14 can then be partially filled with water along with a flower having its stem extending into test-tube 14. Optionally, cap 16 or plug (not shown) can be attached to test-tube 14 and the flower stem inserted through aperture 18. Test-tube 14 can thereafter be slid into elongated member 12.

Alternatively, if a cigar is to be used with my invention instead of a flower, test-tube 14 can be disregarded. A cigar having the appropriate dimensions can be inserted into elongated hollow member 12. An optional cover (not shown) can be used to seal the cigar within elongated member 12 until the cigar is removed.

I claim:

1. A flower holder assembly for use within the interior of an automobile, comprising:

a hollow tubular post member having a circumferential exterior wall surface and adapted to be vertically disposed;

an elongated support member adapted to be horizontally disposed, the support member having one end with a non-conductive surface adapted to be frictionally engaged within a cigarette lighter receptacle of the automobile to be supported thereby;

the other end of the support member being directly and rigidly affixed to the post member on one side of the exterior wall surface thereof, at a location near the vertical center of the post member;

a generally tubular container adapted to be vertically disposed, having a closed lower end, being of such diameter as to be removably received within the hollow interior of the post member, and being of such length as to extend well below the vertical center of the post member;

the tubular container being outwardly flanged at its upper end, and the upper end of the post member being adapted to provide vertical support to the tubular container through its flanged end;

whereby the tubular container may be at least partially filled with water, and a flower may be placed inside it and extending down into the water to protrude above the assembly for visible display;

the post member and the support member being integrally formed of a plastic material, the tubular member having a transparent wall; and the post member having a depiction of a flower permanently affixed to it on the side opposite the support member attachment.

* * * * *